US010213519B2

(12) United States Patent
Seshadri et al.

(10) Patent No.: US 10,213,519 B2
(45) Date of Patent: Feb. 26, 2019

(54) FRAGRANCE DISPENSER FOR AIR FILTER (71) Applicant: 3M INNOVATIVE PROPERTIES COMPANY, St. Paul, MN (US)

(72) Inventors: Kannan Seshadri, Woodbury, MN (US); Neeraj Sharma, Woodbury, MN (US); Le'Bron K. Patterson, Maplewood, MN (US); Jeffrey M. Imsande, Menomonie, WI (US); Nicolas A. Echeverri, Woodbury, MN (US); Joon Chatterjee, Bloomington, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 109 days.

(21) Appl. No.: 15/325,944

(22) PCT Filed: Jul. 14, 2015

(86) PCT No.: PCT/US2015/040388
§ 371 (c)(1),
(2) Date: Jan. 12, 2017

(87) PCT Pub. No.: WO2016/011038
PCT Pub. Date: Jan. 21, 2016

(65) Prior Publication Data
US 2017/0136139 A1 May 18, 2017

Related U.S. Application Data (60) Provisional application No. 62/026,112, filed on Jul. 18, 2014.

(51) Int. Cl.
*A61L 9/04* (2006.01)
*B01D 46/00* (2006.01)
*A61L 9/12* (2006.01)

(52) U.S. Cl.
CPC ............ *A61L 9/12* (2013.01); *B01D 46/0038* (2013.01); *B01D 46/0041* (2013.01); *A61L 9/042* (2013.01);
(Continued)

(58) Field of Classification Search
CPC ............ B01D 46/0038; B01D 46/0041; B01D 2279/50; A61L 9/12; A61L 2209/14
(Continued)

(56) References Cited

U.S. PATENT DOCUMENTS 4,065,262 A * 12/1977 Petroff ................... B01D 46/12
239/289
4,095,031 A 6/1978 Engle
(Continued)

FOREIGN PATENT DOCUMENTS

| EP | 0810885 B1 | 11/2001 |
| EP | 2030638 A1 | 3/2009 |
| FR | 2794405 A1 | 12/2000 |

OTHER PUBLICATIONS

ME 410 Experiment 6 Characteristics of an Airfoil, [online], [retrieved from internet on Jan. 25, 2017], URL < http://www.me.metu.edu.tr/courses/me410/exp6/exp6.html>, 16 pages, date not provided.
(Continued)

*Primary Examiner* — Frank M Lawrence, Jr.
(74) *Attorney, Agent, or Firm* — Kenneth B. Wood (57) ABSTRACT A fragrance dispenser for emitting fragrance into an airstream impinging on an air filter, the dispenser having a receptacle with an open end that faces toward the air filter and that has a porous diffuser layer occlusively overlying the open end of the receptacle.

20 Claims, 2 Drawing Sheets (52) U.S. Cl.
CPC ............... *A61L 9/046* (2013.01); *A61L 9/048* (2013.01); *A61L 2209/131* (2013.01); *A61L 2209/14* (2013.01); *A61L 2209/16* (2013.01); *B01D 2279/50* (2013.01)

(58) Field of Classification Search
USPC .................. 96/222; 239/34, 57; 422/123; 261/DIG. 88
See application file for complete search history.

(56) References Cited

U.S. PATENT DOCUMENTS

| | | | |
|---|---|---|---|
| 4,157,787 A * | 6/1979 | Schwartz | A61L 9/12 |
| | | | 239/56 |
| 4,161,283 A * | 7/1979 | Hyman | A01M 1/2044 |
| | | | 239/55 |
| 4,874,129 A | 10/1989 | DiSapio | |
| 5,087,273 A * | 2/1992 | Ward | B01D 39/00 |
| | | | 239/55 |
| 5,240,487 A * | 8/1993 | Kung | A61L 9/12 |
| | | | 261/DIG. 88 |
| 5,273,690 A * | 12/1993 | McDowell | A61L 9/12 |
| | | | 206/532 |
| 5,478,505 A | 12/1995 | McElfresh | |
| 5,527,493 A | 6/1996 | McElfresh | |
| 5,547,636 A | 8/1996 | Vick | |
| 5,698,166 A * | 12/1997 | Vick | A61L 9/042 |
| | | | 261/30 |
| 6,109,537 A | 8/2000 | Heath | |
| 6,117,218 A * | 9/2000 | Snyder | A61L 9/048 |
| | | | 261/DIG. 17 |
| 6,746,521 B2 | 6/2004 | Canfield | |
| 6,881,776 B2 | 4/2005 | Butuc | |
| 7,754,198 B2 | 7/2010 | Whitehead | |
| 7,833,515 B2 | 11/2010 | Corzani | |
| 8,043,606 B2 | 10/2011 | MacBeath | |
| 8,603,963 B1 | 12/2013 | Steward | |
| 2006/0196964 A1* | 9/2006 | Wheatley | A61L 9/03 |
| | | | 239/57 |
| 2010/0308130 A1 | 12/2010 | Gruenbacher | |
| 2011/0243788 A1 | 10/2011 | Garten | |
| 2011/0278370 A1* | 11/2011 | Glydon | B65D 5/38 |
| | | | 239/6 |
| 2012/0079945 A1 | 4/2012 | Roberts | |
| 2012/0090471 A1* | 4/2012 | Robinson | A61L 9/048 |
| | | | 96/222 |
| 2013/0000489 A1 | 1/2013 | Lu | |
| 2014/0190355 A1 | 7/2014 | Lackey | |

OTHER PUBLICATIONS

International Search Report for PCT International Application No. PCT/US2015/040388 dated Oct. 23, 2015, 3 pages.
Seshadri, U.S. Appl. No. 62/356,668, "Fragrance Dispenser with User-Selectable Release Rate", filed Jun. 30, 2016.
Extended European Search Report, EP15821508.7, dated Mar. 8, 2018, 3 pages.

* cited by examiner

FRAGRANCE DISPENSER FOR AIR FILTER

BACKGROUND

Air filters are often used to reduce the number of particles in a moving airstream, e.g. in residential HVAC (heating-ventilation-air conditioning) systems.

SUMMARY

Herein is disclosed a fragrance dispenser for emitting fragrance into an airstream impinging on an air filter. The dispenser comprises at least one receptacle having a major open end that faces toward the air filter and having a porous diffuser layer occlusively overlying the major open end of the receptacle. Methods of making such a dispenser, and methods of arranging such a dispenser and an air filter are also disclosed. These and other aspects of the invention will be apparent from the detailed description below. In no event, however, should this broad summary be construed to limit the claimable subject matter, whether such subject matter is presented in claims in the application as initially filed or in claims that are amended or otherwise presented in prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", "bottom", "upper", "lower", "under", "over", "front", "back", "outward", "inward", "up" and "down", and "first" and "second" may be used in this disclosure, it should be understood that those terms are used in their relative sense only unless otherwise noted.

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

Figure 4:
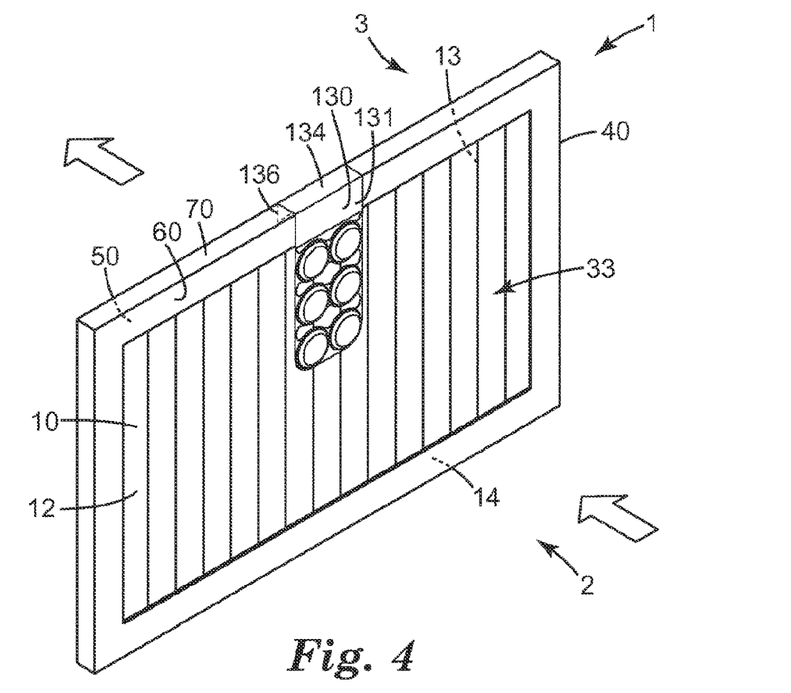
FIG. 4 is a perspective view, generally from the upstream side, of an exemplary framed filter with an exemplary fragrance filter mounted thereon.

The term "upstream" denotes the side of an air filter toward which air flows and against which the airstream impinges when the filter is positioned within a forced-air handling system (e.g., a residential HVAC system); the term "downstream" denotes the side of an air filter through which filtered air exits the filter, both as illustrated in FIG. 4 (in which the large arrows indicate airflow). Similarly, the downstream side of a fragrance dispenser is the side facing at least generally toward the air filter; the upstream side is the side facing at least generally away from the air filter (i.e., that is facing at least generally toward the incoming airstream). The term "lateral" as applied to an air filter means any direction generally in the major plane of the filter as a whole (irrespective of e.g. any pleating that may be present in the filter media); such directions are typically at least generally orthogonal to the direction of the airflow toward the filter. Similarly, the term "lateral" as applied to a fragrance dispenser means any direction generally in the major plane of the fragrance dispenser; such directions may often coincide at least generally with a major plane of a diffuser layer that is present in the dispenser, as discussed in detail herein.

DETAILED DESCRIPTION

Figure 1:
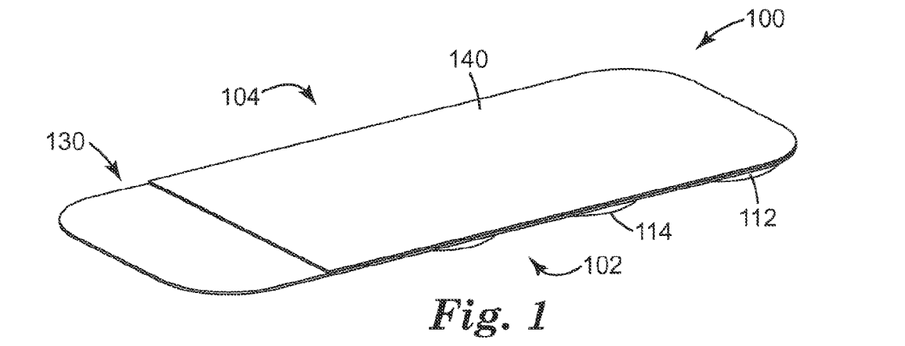
FIG. 1 shows a perspective view, generally from the downstream side, of an exemplary fragrance dispenser as disclosed herein.
Figure 2:
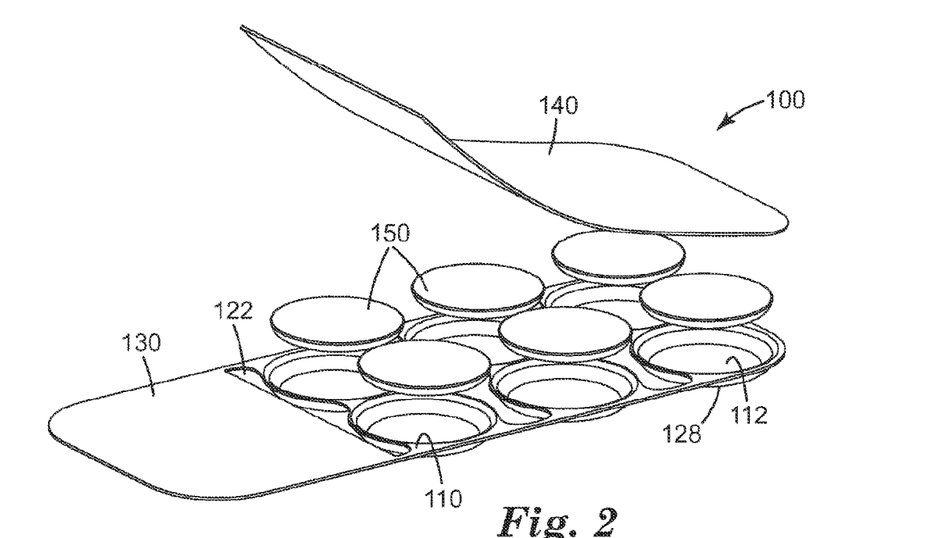
FIG. 2 is an exploded view of the exemplary fragrance dispenser of FIG. 1.

Shown in FIGS. 1 and 2 in exemplary embodiment is a fragrance dispenser 100 comprising an upstream side 102 and a downstream side 104. Dispenser 100 may be at least generally rectangular, or may be elliptical, irregular, etc., in overall shape (as defined e.g. by the lateral perimeter of dispenser 100). Dispenser 100 comprises a base 110 (shown in isolated view in FIG. 3) comprising at least one receptacle 112 with a major closed end 114 and a major open end 116; and, a diffuser layer 140 that occlusively overlies the major open end 116 of the at least one receptacle 112. The at least one receptacle 112 and the diffuser layer 140 (specifically, the portion of a diffuser layer 140 that overlies a particular receptacle 112) combine to define a receptacle volume of the at least one receptacle. A fragrance source 150 is disposed within the at least one receptacle 112. In the illustrated embodiment of FIGS. 1 and 2, a plurality of receptacles 112 is provided (which forms an array of receptacle volumes), each of which is overlain by an area of a single diffuser layer 140. In an alternative embodiment, separate diffuser layers may be provided for each receptacle of an array of receptacles.

Base 110 of dispenser 100 may be provided in any suitable manner. In some embodiments, base 110 may be made of a thermoplastic organic polymer. Conveniently, in such embodiments the at least one receptacle 112 may be provided by forming (e.g., molding, e.g. thermoforming or vacuum-forming) the thermoplastic polymer so as to provide at least one thermoformed depression (as viewed from the downstream side; such a feature will be a protrusion as viewed from the upstream side) 128 in the base. In such an arrangement, an upstream terminus of a depression 128 can provide the major closed end 114 of a receptacle 112 and a major open end of the depression 128 can provide the major open end 116 of the receptacle.

Figure 3:
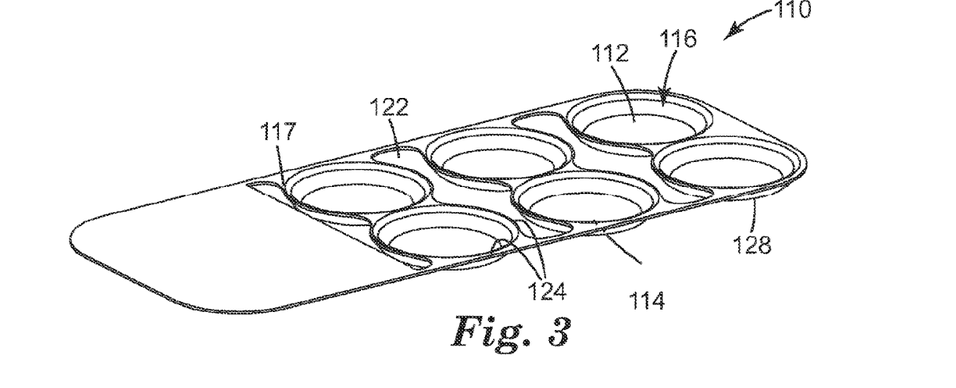
FIG. 3 is an isolated view of an exemplary base of a fragrance dispenser.

In some embodiments, receptacle 112 may take the form of a shallow cavity or basin in base 110 (as illustrated in exemplary embodiment in FIG. 3). Such a shallow cavity may be significantly wider (along at least one lateral dimension that may be at least generally aligned with a major plane of the base) than it is deep (along a dimension at least generally orthogonal to the major plane of the base and that is at least generally aligned with the direction of impinging airflow). In many embodiments, the major open end 116 (which, in use of dispenser 100, may be unobstructed except for the presence of an overlying diffuser layer 140 as discussed later herein) may be similar in lateral size and area to the largest lateral size and area of receptacle 112 (such an arrangement is shown in exemplary embodiment in FIG. 3). In other words, in such embodiments major open end 116 is not in the form of a bottleneck or throat. In specific embodiments, the major open end 116 of a receptacle may exhibit an area that is at least about 70, 80, 90, or 95% of the largest area of the receptacle.

Any number of receptacles (e.g. 2, 3, 4, 5, 6, 8, 10 or more) may be used. In some embodiments, some or all of the receptacles may be at least generally coplanar with each other. Receptacles may be arranged in a regular array, or in an irregular pattern, as desired. Receptacles may all be the same shape, or may differ in shape. An individual receptacle may be e.g. circular, square, triangular, rectangular, or irregular in shape. Individual receptacles may all be the same lateral size, or may differ in size. The lateral size of an individual receptacle (as may be established e.g. by the lateral size of a thermoformed depression in a base, as discussed below) may be e.g. at least about 4, 10, 15, or 20 mm. Such a lateral size may be at most about 40, 35, 30, 25, or 25 mm. (The diameter of a generally circular receptacle, or the equivalent diameter of a noncircular receptacle, may be used as the lateral size of the receptacle.) An individual receptacle may have a depth (from the major closed end 114 to the major open end 116) of at least about 1, 2, 3, 4 or 5 mm. An individual receptacle may have a depth of at most about 20, 15, 12, 10, 8, 6 or 4 mm. The number of receptacles, and/or the depth and lateral size of receptacles, can be chosen to provide the desired total (cumulative) amount of fragrance to be delivered into an airstream. Likewise, at least some such parameters (in particular the ratio of the lateral size of receptacles to the depth of receptacles) can be chosen (e.g. in combination with the porosity of diffuser layer 140) to tailor the rate at which the fragrance is released into the airstream.

In some embodiments, base 110 may be made of a material (e.g., a thermoplastic organic polymer) that is at least substantially impermeable to volatilizable fragrance. By this is meant that the ratio of the rate at which volatilizable fragrance can leave the at least one receptacle by passing through the material of the base, to the rate at which the volatilizable fragrance can leave the at least one receptacle by passing through the diffuser layer, is less than 0.001.

As noted, at least one selected receptacle 112 comprises a porous diffuser layer 140 that occlusively overlies the major open end 116 of the receptacle 112. In this context, to occlusively overlie means that only way that volatilized fragrance can exit receptacle 112 is by passing as a vapor through (the air-filled passages of) diffuser layer 140. In some embodiments, this may be achieved by sealing (e.g., bonding by any suitable means, e.g. via adhesive, heat-sealing, ultrasonic welding, or the like) diffuser layer 140 to a sealing flange 117 that partially or completely laterally surrounds the lateral edges 124 of a receptacle 112.

Diffuser layer 140 is porous, defined herein as meaning that the layer comprises air-filled passageways (e.g., microperforations, interstitial spaces between fibers, interconnected air-filled cells of an open-celled foam, and the like) that extend completely through the diffuser layer from one major surface to another. (It is not necessary, however, that the passageways extend through the layer in a straight line, or along the shortest distance between the major surfaces.) Such air-filled passages allow the passage of volatilized fragrance therethrough in vapor form. Porous diffuser layer 140 will be distinguished from a layer that does not comprise porosity (i.e., a layer in which a small molecule, in order to pass through the layer, must solubilize in the solid material of the layer and then move therethrough by molecular diffusion through the solid material, rather than passing through air-filled passageways).

In at least some embodiments, diffuser layer 140 is at least substantially impermeable to liquids along any dimension thereof. Such a diffuser layer 140, while allowing fragrance molecules in vapor form to pass therethrough so as to exit receptacle 112, may not allow any flow of liquid fragrance (or the liquid form of any other material present in fragrance source 150) e.g. through the thickness of diffuser layer 140 so as to permit the material to escape receptacle 112 in liquid form. In particular embodiments, diffuser layer 140 may not allow any liquid to flow (e.g., by wicking due to capillary action) along the major plane of diffuser layer 140. A porous diffuser layer 140 of this type will be distinguished from e.g. wicking layers and the like that are often used e.g. to facilitate the movement of a liquid through the wicking layer to a location in which the liquid can be volatilized and/or to spread the liquid over a wider area so that is can be more rapidly volatilized.

Diffuser layer 140 may be conveniently provided as a sheet as shown in exemplary embodiment in FIG. 2. Such a sheet may be a film (e.g., a microperforated film, with a microperforation being a through-hole having an average diameter of 400 microns or less), a non-woven or woven material, etc. Such a sheet (e.g. a microperforated film) may thus comprise a number of specific through-holes that pass directly through the thickness of the sheet; or, a sheet (e.g. a non-woven) may comprise tortuous paths (e.g., defined collectively by numerous fibers) through the thickness dimension thereof. Either arrangement (or any combination thereof) may be used as long as the ability to permit passage of vapors therethrough (and the ability to deny flow of liquids therethrough, if desired) is achieved. It will be appreciated that the size (e.g., diameter or effective diameter for circular or non-circular microperforations) or effective size of air-filled passages, as well as the chemical composition of the material of diffuser layer 140, may be chosen to achieve the desired combination of properties. Surface treatments and the like may be used to modify e.g. the surface energy of the microperforations, or of fibers that define a tortuous path, to similar ends.

In particular embodiments, a diffuser layer 140 may be hydrophobic, e.g. by virtue of the composition of the material(s) that makes up the diffuser layer, by virtue of surface treatment, coating or the like that is provided on at least some surfaces of the diffuser layer, or by some combination of these. Such a property may render the diffuser layer resistant to being penetrated e.g. by hydrophilic liquid components of a fragrance source 150 that is in the form of e.g. an aqueous gel. Similarly, in some embodiments, a diffuser layer 140 may be oleophobic (again either through the composition of the material that makes up the diffuser layer, by a surface treatment or coating, or the like). Such a property may render the diffuser layer resistant to being penetrated e.g. by hydrophobic liquid components of a fragrance source that is in the form of e.g. an oil-based gel.

The microperforation size (and/or the effective size of a tortuous path) and/or density of microperforations/paths per unit area of diffuser layer 140 may be tailored to provide a desirable fragrance release rate. Exemplary perforation sizes of microperforated films may be e.g. from about 10 to about 100 microns in diameter (or equivalent diameter in the case of non-circular or irregular microperforations). A nonwoven or woven diffuser layer 140 may be optimized e.g. by controlling fiber diameter, basis weight and solidity and/or thickness, to achieve the desired properties. Such nonwovens may be produced by different methods, such as spunbonds, meltblown, composite methods such as spunbond-meltblown-spunbond (SMS), etc. Film materials and/or fibers of a woven or nonwoven fibrous layer may be chosen from any suitable material, e.g. polyolefins such as polyethylene and polypropylene, polyvinyl chloride, polyester, polyurethane, and so on. In at least some embodiments, diffuser layer 140 is not a rupturable membrane that is configured to be ruptured to initiate the release of fragrance therethrough.

Fragrance source 150 may include any suitable volatilizable fragrance or any combination of two or more fragrances. Such a fragrance may be chosen to impart a pleasing odor, to mask odors that are perceived as undesirable, and so on. In some embodiments, fragrance source 150 may comprise one or more fragrances as neat fragrance liquids unmixed with any other material. However, in many embodiments it may be convenient to mix the at least one volatile fragrance with at least one non-volatile carrier material (with the term non-volatile meaning that in use of fragrance dispenser 100, the ratio of the rate at which the carrier material exits the receptacle through the diffuser layer to the rate at which the volatile fragrance exits, is less than 0.001.)

A non-volatile carrier material may be chosen from any suitable material. In various embodiments, such a carrier material may comprise an organic polymeric material (which, in this context, includes e.g. waxes, oils, etc. as long as such materials provide acceptable properties). Such a carrier material may advantageously provide that fragrance source 150 is in the form of a viscous liquid, gel, grease, jelly, semi-solid, wax, or the like (noting that there may not necessarily be a firm dividing line between some of these categories), in the typical temperature ranges at which the fragrance dispenser is used. (The latter temperatures are often in the range of those found in a typical conditioned space; e.g. between 18 and 25° C.)

In further detail, a non-volatile carrier (e.g., a polymeric material) may provide a matrix for dispersal of the fragrance thereinto. In some embodiments, the at least one volatile fragrance and the at least one non-volatile carrier material may be mixed with each other to form a solution (i.e., so that substantially no parcels of non-dissolved volatile fragrance are present). Exemplary organic polymers that may find use as non-volatile carriers include e.g. olefinic copolymers, e.g. copolymers of polyethylene with ethylene methyl acrylate (for example the resins available from Exxon Mobil under the trade designations OPTEMA 120 and 220), ethylene vinyl acetate (EVA), or other copolymers containing other functional groups such as acids, esters, amides, acrylates, and the like. In addition, the organic polymer system could be comprised of styrene-isoprene-styrene segments or styrene—butadiene-styrene segments such as those seen in Kraton thermoplastic elastomer systems. Fragrance source 150 may comprise (either instead of, or in addition to, any non-volatile organic polymer that may be present) any suitable inorganic material such as e.g. clay, fumed silica, diatomaceous earth, silica aerogels, and so on.

Fragrance source 150 may also comprise any other agent as desired to change the viscosity, tackiness or any other characteristic of the fragrance source. (Such agents may be non-volatile or volatile.) Viscosity modifiers include plasticizers such as isopropyl myristate, heavy naphthenic oils, or other polymeric systems that may be branched, linear, dendritic, and so on. Tackifiers include Wingtack Plus and the like. If desired, one or more gelling agents may be used, e.g. wax esters such as those available from Croda, Edison, N.J. under the trade designation SYNCROWAX, and acrylate containing polymers, such as those available from Air Products, Allentown, Pa. under the trade designation INTELLIMER. Such components may be used to provide e.g. an oil-based gel. In some embodiments, gelling agents such as e.g. crosslinked polysaccharides, starches, alginates, carrageenan, and the like, may be used to provide a fragrance source in the form of an aqueous or aqueous-containing gel. Any fragrance source may of course comprise any desired combination of hydrophobic and hydrophilic components, for any purpose, as desired. Components of a fragrance source 150 may be chosen so as to render the volatile fragrance completely mixed (e.g., solubilized) with the other components without any partitioning or phase separation, and also to prevent or minimize any syneresis of liquid fragrance (or any other component) therefrom. In various embodiments, fragrance source 150 may exhibit a viscosity at 25° C. of at least about 10, 20, 40, 80, 200, 400, 1000, or 2000 Poise.

In some embodiments, fragrance source 150 may comprise at least one colorant (e.g., dye). A colorant may be volatile (e.g. guaiazulene dye) e.g. with an evaporation rate similar to that of the volatile fragrance, so that release of the dye from the fragrance source causes a color change in the fragrance source that is commensurate with the depletion of fragrance from the fragrance course. Or, a colorant may be non-volatile, and the non-volatile colorant, the volatile fragrance, and e.g. the non-volatile carrier material may be chosen in combination so that release of the fragrance from the fragrance source causes the color of the fragrance source to change so that depletion of the fragrance from the fragrance source can be monitored. In either case, at least a portion of base 110 that defines a major closed end 114 of a receptacle 112 may be at least translucent or transparent, so that any change in color of the fragrance source may be visually observed through the base.

The volatile fragrance can be combined with the non-volatile carrier material (and with any other component) in any desired ratio. In various embodiments, the volatile fragrance may comprise at least about 30, 50, 60, 70, 80, or 90 wt. % of the fragrance source. In further embodiments, the volatile fragrance may comprise at most about 90, 80, 70, 60, 50, or 40 wt. % of the fragrance source. The fragrance may be combined with other components, e.g. a non-volatile carrier, by batch mixing, by compounding in an extruder, or in general by any process that homogenizes the fragrance within the matrix. The compounded mixture may be loaded into a receptacle or receptacles to therein provide a fragrance source. If desired, the compounded mixture may be heated slightly to facilitate loading of the mixture into a receptacle.

In some embodiments, fragrance source 150 may occupy at least about 70, 80, 90, 95, or 98 volume percent of the receptacle volume, the receptacle volume being defined in combination by the open-ended receptacle 112 (e.g., by the downstream surfaces of the molded depression 128) and the overlying diffuser layer 140. In specific embodiments, at least a portion of a downstream major surface of fragrance source 150 is in intimate contact with an upstream surface of diffuser layer 140. In some embodiments, the receptacle may include a space-filling network (e.g. an open-cell foam, a reticulated foam, a non-woven, a netting, a collection of particulates or the like, that occupies a portion of the receptacle volume and that comprises numerous open-ended cavities that may collectively provide a reservoir for the fragrance source. If desired, a fragrance source may be pre-loaded into a space-filling network, which network is then placed into a receptacle 112 that is sized and shaped to accept the space-filling network. Exemplary foams may be constructed out of polyethylene, polyurethane, PVC and the like. Exemplary non-wovens and particulates may be those that are manufactured to be sorbents, such as those manufactured for chemical spill clean up, e.g., 3M Petroleum Sorbent pads available from 3M Company, St. Paul, Minn. In at least some embodiments, fragrance source 150 as provided in receptacle 112, is not contained within any kind of secondary container or barrier, in particular a rupturable barrier, within receptacle 112.

A volatile fragrance may be any molecule or mixture of different molecules that may impart a pleasing odor, that may mask odors that are perceived as undesirable, and so on. Any such molecule may be chosen from those compounds commonly referred to as perfumes, aroma compounds, aromatherapy compounds, odorants, flavors, essential oils, and so on. Such molecules will exhibit the appropriate vapor pressure at the temperatures usually encountered in e.g. residential HVAC systems (e.g., 18-25° C.) to function as desired. In various embodiments, a volatile fragrance may comprise a molecular weight (of a single molecule) or an average molecular weight (for mixtures of molecules of different molecular weights), of less than about 500, 400, 300, or 200. Various volatile fragrances and categories thereof are disclosed in U.S. Pat. No. 8,043,606 to MacBeath, which is incorporated by reference herein. In particular embodiments in which an array of receptacles 112 is present, different fragrances and/or mixtures thereof may be present in the various receptacles, as desired.

Fragrance dispenser 100 may be used with any suitable air filter. Shown in FIG. 4 in perspective view generally from the upstream side, is an exemplary air filter 1 along with an exemplary fragrance dispenser 100 as disclosed herein, viewed from the upstream side of air filter 1 and dispenser 100. Exemplary air filter 1 is a framed air filter, comprising air filter media 10 and support frame 40 mounted on the perimeter of air filter media 10. Air filter 1 may conveniently be generally rectangular in shape (which includes square shapes), with air filter media 10 likewise being generally rectangular and with support frame 40 taking the form of a rectangular frame mounted to (e.g., attached to) the perimeter of air filter media 10.

Air filter 1 comprises an airstream-receiving area 33, meaning an area of filter media 10 that is not covered or blocked by perimeter frame 40 (such an area is typically laterally surrounded by perimeter frame 40); this will be recognized as the "active" filtering area of the air filter. Air filter media 10 in airstream-receiving area 33 has an upstream face 12 on upstream side 2 of air filter 1, and a downstream face 13 on downstream side 3 of air filter 1. Air filter media 10 is typically sheet-like, with a length and width that are greater than the thickness of the air filter media and with an overall planar configuration with a distinguishable major plane thereof. In some embodiments, air filter media 10 is a pleated material (which media will still exhibit an overall major plane notwithstanding the superposition of pleating thereupon). By "pleated" is meant a web at least portions of which have been folded to form a configuration comprising rows of generally parallel, oppositely oriented folds. As such, the pleating of a web is distinguished from e.g. the crimping of individual fibers. In some embodiments, air filter media 10 is a pleated material that comprises a highly open wire mesh or screen that is bonded to the air filter media in order to enhance the pleatability thereof and that is pleated along with the air filter media itself. Although FIG. 4 illustrates an air filter 1 comprising pleated air filter media 10, any suitable non-pleated (e.g., generally flat) air filter media may be used. Air filter media 10, whether pleated or in substantially flat state or otherwise, may comprise open cell structures, porous layers, or the like, any of which can comprise any suitable material, chosen from e.g. porous foams, non-wovens, papers, fiberglass, or the like, alone or in combination with one another.

In some embodiments, a support frame 40 may be mounted on perimeter 14 of air filter media 10. In some embodiments, frame 40 comprises a channel frame (e.g., a generally U-shaped frame) comprising an upstream flange 60 at least an inwardmost portion of which is positioned in overlapping relation to, and upstream of, at least perimeter 14 of air filter media 10, as may be seen most easily e.g. in FIG. 4. Channel frame 40 may further comprise downstream flange 50 (not visible in FIG. 4), at least an inwardmost portion of which is positioned in overlapping relation to, and downstream of, at least perimeter 14 of air filter media 10. U-shaped channel frame 40 may further comprise sidewall 70, which outwardly bounds air filter media 10. (Sidewall 70 may thus comprise the base of a U-shaped frame, with upstream and downstream flanges 60 and 50 comprising the arms of the U-shaped frame.)

In some embodiments, a support frame may be a pinch frame. In such embodiments, at least a portion of a flange (e.g., a downstream flange 50) that is distal to sidewall 70 of frame 40, may be pinched toward the other flange (e.g., upstream flange 60) of the frame. Such a pinched flange may provide a truss construction that provides additional support. In some embodiments, at least the downstream side of air filter 1 may comprise any desired reinforcing structure, such as e.g. a support grill, and/or one or more reinforcing strips, beams, members, sheets, scrims, strands, filaments, or the like that may extend across at least a portion of active area 33 of the filter media.

Fragrance dispenser 100 is configured to be placed in proximity to air filter 1 so that receptacle 112 (or, an array of multiple receptacles 112 if present) is proximate the airstream-receiving area 33 of the upstream face 12 of the upstream side 2 of the air filter. In some embodiments, fragrance dispenser may be attached to, e.g. suspended from, a wall of a duct within which air filter 1 is positioned, in such manner as to place dispenser 100 proximate area 33 of the air filter. However, in many embodiments it may be convenient to mount dispenser 100 on the air filter itself (e.g., to attach dispenser 100 to the air filter) to achieve the desired positioning. In a slight variation, the air filter itself, and a component of the duct within which the air filter is positioned, may combine to hold dispenser 100 in the desired location. For example, a mounting mechanism of dispenser may have a portion that is e.g. sandwiched between the air filter and a surface of a receiving slot in the duct that receives the air filter, as discussed later herein.

However achieved, fragrance dispenser 100 is placed so that receptacle 112 (or, an array of multiple receptacles 112 if present) is proximate the airstream-receiving area 33 of the air filter. In this context, by proximate is meant that receptacle 112 is less that 4 cm upstream of filter media 10 of airstream-receiving area 33, at their point of closest approach. In further embodiments, the distance of closest approach between receptacle(s) 112 and filter media 10 of airstream-receiving area 33, may be less than about 3, 2, or 1 cm.

By these arrangements, receptacle(s) 112 is exposed to the moving air of the airstream as the airstream approaches the upstream face 12 of the air filter. And, dispenser 100 is oriented so that the major closed end 114 of the at least one receptacle 112 faces at least generally upstream (toward the incoming airstream) and the major open end 116 of the receptacle faces at least generally downstream (i.e., toward the upstream face 12 of the airstream-receiving area 33 of the filter media 10.). By at least generally upstream/downstream is respectively meant within plus or minus 45 degrees of facing strictly upstream/downstream, as measured by way of comparing the airflow direction that is orthogonal to the major plane of the air filter, to an axis that is orthogonal to a major plane of the receptacle (such a major plane of the receptacle will often be parallel to a major plane of the diffuser layer 140 that overlies the receptacle). In further embodiments, the dispenser is oriented so that the major closed end and major open end of the at least one receptacle, are respectively aligned within 30, 20, 10, or 5 degrees of facing strictly upstream and downstream.

Figure 5:
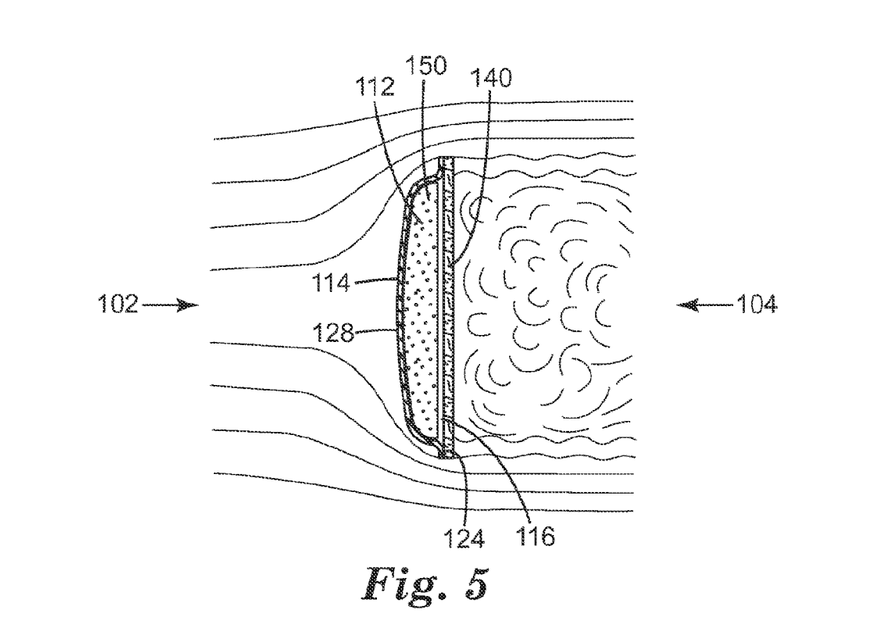
FIG. 5 depicts a side view of airflow around an exemplary receptacle and diffuser layer of a fragrance dispenser.

Arranging a fragrance dispenser in this manner can provide that (considering for the moment a single receptacle) the incoming airstream will impinge on the upstream surface of (air-impermeable) major closed end 114 of the receptacle and be blocked and deflected laterally so as to follow the contours of the upstream surface of the receptacle and will then pass around the lateral edges 124 of the receptacle as the airstream continues toward area 33 of the filter. Such a flow arrangement is depicted in idealized representation in FIG. 5. It will be appreciated that such an arrangement may place major open end 116 of the receptacle, and diffuser layer 140 that overlies the major open end, in an airflow "shadow" as shown in FIG. 5. This may cause a turbulent wake (in the otherwise laminar flow that is typically found in well-developed flow in e.g. residential air ducts) and/or a region of decreased pressure immediately adjacent to (downstream of) the major open end/diffuser layer.

Although not wishing to be limited by theory or mechanism, such an arrangement may provide that the mass transfer of volatilized fragrance through the diffuser layer and into the airstream may at least generally follow zero-order kinetics. This may provide that, over at least a significant fraction of the useful lifetime of the dispenser, the release of volatilized fragrance from the receptacle may be at least generally, or even substantially, independent of the amount or concentration of fragrance remaining in the receptacle. Such an arrangement may be contrasted e.g. with an arrangement in which an airstream either impinges directly on or sweeps directly alongside a mass-transfer boundary (such as provided by a diffuser layer) rather than the mass-transfer boundary being in an airflow "shadow" as described above.

The ordinary artisan will appreciate that arrangements as disclosed herein, which may at least generally approach zero-order kinetics, may provide relatively steady and sustained release of fragrance for prolonged periods of time. Such a result may be advantageous over airflow arrangements that release fragrance according to first-order (or higher-order) mass transfer regimes and that may initially release fragrance at a high rate (e.g., in an initial burst) followed by a steep falloff in the rate of fragrance released.

It will also be appreciated that the arrangements disclosed herein, relying on the release of fragrance from a receptacle by way of the fragrance passing through the air that is present in air-filled passageways of a porous layer, are distinguished from arrangements that rely on the release of volatilized fragrance from a receptacle by way of molecules of fragrance solubilizing in the solid material of a nonporous layer and then moving through the layer by molecular diffusion through the solid material of the layer.

To enhance the airflow effects discussed above (particularly in the case that a dispenser 100 comprises an array of multiple receptacles), one or more through-holes may be provided in base 110 of dispenser 100. An array of multiple through-holes are most clearly visible in the isolated view of exemplary base 110 in FIG. 3. Any such a through-hole will extend completely through the thickness (the shortest dimension) of the base in an upstream-downstream direction so as to permit the flow of air therethrough. In various embodiments, one through hole (or multiple through-holes acting collectively) may be present, and may provide that a receptacle exhibits a lateral edge 124 that is an exposed lateral edge over a circumferential extent of at least about 30, 40, 50, 60, or 70% of the receptacle. (In this context, it is noted that the term circumferential extent is used for convenience and does not necessitate that a receptacle must have a purely circular geometry.) Such an exposed lateral edge is any edge portion (segment) that is not bordered by any solid material (e.g., by an adjacent receptacle or by an extending portion of base 110, both of which features can be found in FIG. 3) that extends more than 2 mm laterally away from that lateral edge portion. It will be understood that an exposed lateral edge may be provided e.g. by either a through-hole, or by a terminal edge of the dispenser itself (both types of features are evident in FIG. 3). By way of specific example, the exemplary receptacles 112 of FIG. 3 each comprise an exposed lateral edge over an estimated circumferential extent of approximately 80% of the receptacle. In the case where the diffuser layer 140 is provided as a sheet that extends over e.g. the entire face of the dispenser 100, cutouts may be provided in the diffuser layer 140 that substantially correspond with the cutouts in base 110. Alternatively, diffuser layer 140 may be constructed so as to be consistent of multiple suitably shaped pieces of the diffuser material arranged and attached in a largely co-planar fashion to the base 110 so as to maintain the openness of the through-holes in base 110.

Dispenser 100 may be mounted on an air filter 1 by way of any suitable mechanism. Many such mechanisms may conveniently make use of a perimeter frame (e.g., a rigid perimeter frame such as made from cardboard, chipboard or the like) for such mounting. In some embodiments, base 110 of dispenser 100 may comprise a main body that comprises the at least one receptacle 112; and, an extended portion 130 (as shown in exemplary embodiment in FIG. 3) that extends away from the main body. Extended portion 130 may comprise any suitable mounting mechanism configured to mount (attach) to a perimeter frame 40 of an air filter 1 so as to position fragrance dispenser 100 so that the at least one receptacle 112 is proximate the airstream-receiving area 33 of the upstream face 12 of the air filter.

In many embodiments, extended portion 130 may be configured to abut an upstream flange 60 of perimeter frame 40 when dispenser 100 is mounted on air filter 1. In some embodiments, an extended portion 130 may comprise pressure-sensitive adhesive with a first major side that is adhesively attached to the extended portion and with a second major side that is configured to adhesively attach to an upstream flange 60 of a perimeter frame 40 of an air filter 1. The lateral length of extended portion 130, and the lateral extent of a frame flange 60, may be chosen so that when extended portion 130 is adhesively attached to a frame, the at least one receptacle 112 is satisfactorily placed in proximity to the airstream-receiving area 33 of the filter.

Instead of or as an adjunct to an adhesive, extended portion 130 may comprise any mounting/attachment mechanism that may be used in combination with a mounting/attachment feature provided on perimeter frame 40. For example, a small protrusion or stud may be provided on upstream flange 60 of frame 40, with a corresponding hole being provided in extended portion 130 of dispenser 100 (or, vice versa). It will be understood that this is merely an example and that many mounting attachment systems may be used, such as hook-and-loop mechanisms, mating extruded structures such as Dual Lock reclosable fasteners (3M Company) and the like. Moreover, such attachment systems do not necessarily have to be already attached to dispenser 100 (or to filter 1) as provided. For example, an S-hook may be used with one end that passes through a receiving aperture in extended portion 130 of dispenser 100 (or, that passes through a through-hole 122 in the main body of base 110) and with another end that hooks over the top of a perimeter frame 40. In another embodiment the S-hook may be attached to the filter media 10 in the airstream-receiving area 33 so that the at least one receptacle 112 is satisfactorily placed in proximity to the airstream-receiving area 33 of the filter. In another embodiment, the extended portion 130 of dispenser 100 may be provided with 2 through-holes close to each other so as to allow a U-shaped wire to be passed through the holes in dispenser 100 and correspondingly through the filter media 10 in the airstream-receiving area 33 of the filter and be suitably twisted at the opposite face of the filter.

In some embodiments, an extended portion 130 may generally comprise an L-shape with a first portion (131 of FIG. 4) that extends from the main body of base 110 in a direction at least generally along a major plane of the main body of the base, and a second portion 134 that extends from a terminus of the first portion (i.e., from a terminus that is distal from the attachment point of the first portion to the main body). Second portion 134 may be oriented at least generally orthogonally to first portion 131, and may comprise a major surface that is configured to abut a sidewall 70 of perimeter frame 40 of the air filter (both such features are shown in FIG. 4). In such embodiments, either or both of first portion 131 and second portion 134 may comprise a pressure-sensitive adhesive (or any other attachment mechanism) whereby they can be respectively attached to upstream flange 60 and sidewall 70.

In further embodiments, the extended portion 130 may comprise first and second portions 131 and 134 as described above, and may further comprise a third portion 136 (not visible in FIG. 4) that extends from a terminus of the second portion 134 (i.e., from a terminus that is distal from the attachment point of the second portion to the first portion). Such a third portion 136 may comprise a major plane that is oriented at least generally parallel to a major plane of first portion 131, the first and third portions being connected by the second portion 134 such that extended portion 130 may generally comprise a U-shape (with second portion 134 forming the base of the "U"). In such case the third portion 136 may be configured to abut a downstream flange 50 of perimeter frame 40 when dispenser 100 is mounted on air filter 1.

In many embodiments, it may be convenient to mount dispenser 100 on an upper portion of perimeter frame 40 (as in the exemplary arrangement of FIG. 4) so that gravity may assist in holding dispenser 100 in place). In at least some embodiments, either or both of a first portion 131 and a third portion 136, may be held (e.g., pinched) between a corresponding flange of the perimeter frame of the air filter, and a flange, edge, etc., of a receiving slot into which the air filter is placed.

An air filter 1 and a fragrance dispenser 100 may be used in combination to form an assembly which may release fragrance into a moving airstream. Although the term "assembly" is used for convenience, it will be understood that, strictly speaking, the dispenser and the air filter need not necessarily be attached to each other—as mentioned, a dispenser may be e.g. attached to a duct immediately upstream of the air filter.

In some embodiments, an assembly may be provided to an end user comprising an air filter 1 with a fragrance dispenser 100 already mounted thereon. Or, one or more fragrance dispensers may be provided separately, to be mounted to an air filter (or e.g. mounted on a duct wall) by an end user. In some embodiments, a dispenser 100 may be mounted to an air filter or to a duct wall with the filter already in place (e.g., in a duct of an HVAC system), if the HVAC system permits such access. Alternatively, a dispenser may be mounted to an air filter and the air filter/dispenser assembly then put in place in the duct. It will be appreciated that a rounded upstream surface of the receptacles (as exemplified in FIG. 1) may help the ability to e.g. slide an air filter into place in the duct, with a dispenser thereto. That is, such features may allow the dispenser to easily slide by e.g. an edge of a flange of an air-filter-receiving slot. Also, the main body of the dispenser may be momentarily slightly pushed into the air filter media (e.g., in a downstream direction) to facilitate the inserting of the air filter into the duct.

In some embodiments, a fragrance dispenser 100 a supplied to a user may comprise a vapor-impermeable cover sheet that overlies the porous diffuser layer 140 at least in the areas where diffuser layer 140 overlies the receptacle(s) 112. This may minimize or prevent any loss of fragrance from fragrance source(s) 150, until dispenser 100 is ready to be used. Such a cover sheet may be removed and disposed or recycled at that time. In the case that an array of receptacles 112 is used, a single cover sheet may be provided that may be removed to activate all of the receptacles at once. Or, multiple cover sheets may be used (e.g. in combination with different fragrances in different receptacles); individual cover sheets could then be removed at intervals to release different fragrances in succession over a period of time. In addition, multiple cover sheets may be used to control the number of receptacles 112 activated so as to control the total amount of fragrance released from the array of open receptacles 112. In another embodiment, an attached sliding cover sheet may be provided that can be moved while remaining attached to the dispenser 100 so as to open receptacle(s) 112 in a controlled (and reversible) manner.

If desired, an area (e.g., of an extended portion 130) may be allocated for marking (e.g., writing) by the end user to record the date at which the fragrance dispenser and/or the air filter itself) began use. And, although a dispenser 100 may often be used e.g. with a disposable/recyclable air filter, in some embodiments dispenser 100 may be used with a washable filter, a permanently installed filter, etc. Although discussions herein have focused primarily on use of dispenser 100 with residential HVAC filters, the term air filter is used broadly herein, and dispenser 100 may be advantageously positioned upstream of air filters used with industrial/commercial HVAC systems, room air purifiers, HVAC or cabin air filters for vehicles, and so on.

LIST OF EXEMPLARY EMBODIMENTS

Embodiment 1 is a fragrance dispenser configured to emit fragrance into an airstream flowing toward an airstream-receiving area of an upstream face of an air filter, the dispenser comprising: a base comprising at least one receptacle with a major closed end and a major open end; a porous diffuser layer occlusively overlying the major open end of the at least one receptacle; and, a fragrance source provided within at least a portion of the receptacle and that comprises at least one volatilizable fragrance, wherein the fragrance dispenser is configured to be positioned so that the at least one receptacle is proximate the airstream-receiving area of the upstream face of the air filter, with the major closed end of the receptacle facing at least generally upstream and with the major open end of the receptacle facing at least generally downstream toward the upstream face of the filter.

Embodiment 2 is the fragrance dispenser of embodiment 1 wherein at least the portion of the diffuser layer that occlusively overlies the major open end of the at least one receptacle, is permeable to vapors but is at least substantially impermeable to liquids. Embodiment 3 is the fragrance dispenser of embodiment 2 wherein the diffuser layer is configured so that liquids cannot wick in any direction at least generally along a major plane of the diffuser layer. Embodiment 4 is the fragrance dispenser of any of embodiments 1-3 wherein the base comprises a thickness and comprises at least one through-hole that extends completely through the thickness of the base so as to permit the flow of air therethrough and wherein the at least one receptacle comprises an exposed lateral edge over a circumferential extent of the receptacle of at least about 60%.

Embodiment 5 is the fragrance dispenser of any of embodiments 1-4 wherein the base is made of a thermoplastic organic polymer and wherein the receptacle is provided by a thermoformed depression in the base, wherein an upstream terminus of the depression provides the major closed end of the at least one receptacle and wherein a major open end of the depression provides the major open end of the at least one receptacle. Embodiment 6 is the fragrance dispenser of any of embodiments 1-5 wherein the base is made of a thermoplastic molding resin that is at least substantially impermeable to liquids and vapors.

Embodiment 7 is the fragrance dispenser of any of embodiments 1-6 wherein: the base comprises a plurality of receptacles, wherein at least selected receptacles each comprise: a major closed end and a major open end; a porous diffuser layer occlusively overlying the major open end of the receptacle; and, a fragrance source provided within at least a portion of the receptacle, and, wherein the fragrance dispenser is configured to be positioned so that the at least selected receptacles are proximate the airstream-receiving area of the upstream face of the air filter, with the major closed end of each receptacle facing at least generally upstream and with the major open end of each receptacle facing at least generally downstream toward the upstream face of the filter. Embodiment 8 is the fragrance dispenser of embodiment 7 wherein the base comprises a thickness and comprises a plurality of through-holes that each extend completely through the thickness of the base so as to permit the flow of air therethrough and wherein at least selected receptacles each comprises an exposed lateral edge over a circumferential extent of the receptacle of at least about 60%.

Embodiment 9 is the fragrance dispenser of any of embodiments 1-8 wherein the base comprises a mounting mechanism configured to mount the fragrance dispenser on the air filter so that the at least one receptacle is proximate the airstream-receiving area of the upstream face of the air filter. Embodiment 10 is the fragrance dispenser of embodiment 9 wherein the base comprises a main body that comprises the at least one receptacle and wherein the base further comprises an extended portion that extends away from the main body and that comprises the mounting mechanism, wherein the mounting mechanism is configured to mount to a perimeter frame of the air filter so as to position the fragrance dispenser so that the at least one receptacle is proximate the airstream-receiving area of the upstream face of the air filter. Embodiment 11 is the fragrance dispenser of embodiment 10 wherein the extended portion comprises a pressure-sensitive adhesive with a first major side that is adhesively attached to the extended portion and with a second major side that is configured to adhesively attach to an upstream flange of the perimeter frame of the air filter.

Embodiment 12 is the fragrance dispenser of any of embodiments 10-11 wherein the extended portion comprises an L-shape with a first portion that extends from the base in a direction at least generally along a major plane of the base, and a second portion that extends from a terminus of the first portion and that is oriented at least generally orthogonally to the first portion, and wherein the second portion comprises a major surface that is configured to abut a sidewall of the perimeter frame of the air filter. Embodiment 13 is the fragrance dispenser of any of embodiments 10-11 wherein the extended portion comprises a U-shape with a first portion that extends from the base in a direction at least generally along a major plane of the base, a second portion that extends from a terminus of the first portion and that has a major plane that is oriented at least generally orthogonally to the first portion, and a third portion that extends from a terminus of the second portion and that has a major plane that is oriented at least generally parallel to a major plane of the first portion, wherein the second portion comprises a major surface that is configured to abut a sidewall of the perimeter frame of the air filter and wherein the third portion comprises a major surface that is configured to abut a downstream flange of the perimeter frame of the air filter.

Embodiment 14 is the fragrance dispenser of any of embodiments 1-13 wherein the fragrance source comprises at least one volatile fragrance that is mixed with at least one non-volatile carrier material, wherein the volatile fragrance comprises at least about 80 wt. % of the fragrance source. Embodiment 15 is the fragrance dispenser of embodiment 14 wherein the non-volatile carrier material comprises an organic polymeric material. Embodiment 16 is the fragrance dispenser of any of embodiments 14-15 wherein the receptacle and the diffuser layer combine to define a receptacle volume and wherein the fragrance source occupies at least 95% by volume of the receptacle volume. Embodiment 17 is the fragrance dispenser of any of embodiments 14-16 wherein the at least one volatile fragrance and the at least one non-volatile carrier material are mixed with each other to form a solution with substantially no parcels of non-dissolved volatile fragrance being present.

Embodiment 18 is an assembly comprising a framed air filter and at least one fragrance dispenser mounted in proximity thereto, the assembly comprising: a framed air filter with a perimeter frame, an upstream face with an airstream-receiving area and a downstream face, and, a fragrance dispenser comprising: a base comprising at least one receptacle with a major closed end and a major open end; a porous diffuser layer occlusively overlying the major open end of the at least one receptacle; and, a fragrance source provided within at least a portion of the receptacle and that comprises at least one volatilizable fragrance, wherein the fragrance dispenser is positioned so that the at least one receptacle is proximate the airstream-receiving area of the upstream face of the air filter, with the major closed end of the receptacle facing at least generally upstream and with the major open end of the receptacle facing at least generally downstream toward the upstream face of the filter.

Embodiment 19 is the assembly of embodiment 18 wherein the air filter and fragrance dispenser are configured so that when an airstream is impinged on the airstream-receiving area of the upstream face of the air filter, a major plane of the diffuser layer is at least generally orthogonal to the direction of the airstream flow. Embodiment 20 is the assembly of embodiment 19 wherein the air filter and fragrance dispenser are configured so that when the airstream is impinged on the airstream-receiving area of the upstream face of the air filter, a portion of the airstream that flows toward the airstream-receiving area of the upstream face of the air filter, impinges on the closed end of the receptacle and flows at least generally laterally outward so as to pass laterally around lateral edges of the at least one receptacle before continuing to flow toward upstream face of the air filter. Embodiment 21 is the assembly of embodiment 20 wherein the airflow passing laterally around lateral edges of the at least one receptacle causes the fragrance to be released through the diffuser layer and removed into the airstream, in a zero-order kinetic regime in which the rate of removal of the fragrance from the receptacle is at least generally independent of the amount of fragrance remaining in the receptacle.

Embodiment 22 is an assembly comprising a framed air filter and at least one fragrance dispenser of any of embodiments 1-17 mounted in proximity thereto, the assembly comprising; a framed air filter with a perimeter frame, an upstream face with an airstream-receiving area and a downstream face, and, a fragrance dispenser of any of embodiments 1-17, comprising: a base comprising at least one receptacle with a major closed end and a major open end; a porous diffuser layer occlusively overlying the major open end of the at least one receptacle; and, a fragrance source provided within at least a portion of the receptacle and that comprises at least one volatilizable fragrance, wherein the fragrance dispenser of any of embodiments 1-17 is positioned so that the at least one receptacle is proximate the airstream-receiving area of the upstream face of the air filter, with the major closed end of the receptacle facing at least generally upstream and with the major open end of the receptacle facing at least generally downstream toward the upstream face of the filter.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). Although various theories and possible mechanisms may have been discussed herein, in no event should such discussions serve to limit the claimable subject matter. To the extent that there is any conflict or discrepancy between this specification as written and the disclosure in any document incorporated by reference herein, this specification as written will control.

What is claimed is:

1. An assembly comprising a framed air filter and at least one fragrance dispenser mounted in proximity thereto, the assembly comprising;
   a framed air filter with a perimeter frame, an upstream face with an airstream-receiving area and a downstream face,
   and,
   a fragrance dispenser comprising:
      a base comprising at least one receptacle with a major closed end and a major open end;
      a porous diffuser layer occlusively overlying the major open end of the at least one receptacle;
      and,
      a fragrance source provided within at least a portion of the receptacle and that comprises at least one volatilizable fragrance,
      wherein the fragrance dispenser is positioned so that the at least one receptacle is proximate the airstream-receiving area of the upstream face of the air filter, with the major closed end of the receptacle facing at least generally upstream and with the major open end of the receptacle facing at least generally downstream toward the upstream face of the filter.

2. The assembly of claim 1 wherein the air filter and fragrance dispenser are configured so that when an airstream is impinged on the airstream-receiving area of the upstream face of the air filter, a major plane of the diffuser layer is at least generally orthogonal to the direction of the airstream flow.

3. The assembly of claim 2 wherein the air filter and fragrance dispenser are configured so that when the airstream is impinged on the airstream-receiving area of the upstream face of the air filter, a portion of the airstream that flows toward the airstream-receiving area of the upstream face of the air filter, impinges on the closed end of the receptacle and flows at least generally laterally outward so as to pass laterally around lateral edges of the at least one receptacle before continuing to flow toward upstream face of the air filter.

4. The assembly of claim 3 wherein the airflow passing laterally around lateral edges of the at least one receptacle causes the fragrance to be released through the diffuser layer and removed into the airstream, in a zero-order kinetic regime in which the rate of removal of the fragrance from the receptacle is at least generally independent of the amount of fragrance remaining in the receptacle.

5. The fragrance dispenser of claim 1 wherein at least the portion of the diffuser layer that occlusively overlies the major open end of the at least one receptacle, is permeable to vapors but is at least substantially impermeable to liquids.

6. The fragrance dispenser of claim 5 wherein the diffuser layer is configured so that liquids cannot wick in any direction at least generally along a major plane of the diffuser layer.

7. The fragrance dispenser of claim 1 wherein the base comprises a thickness and comprises at least one through-hole that extends completely through the thickness of the base so as to permit the flow of air therethrough and wherein the at least one receptacle comprises an exposed lateral edge over a circumferential extent of the receptacle of at least about 60%.

8. The fragrance dispenser of claim 1 wherein the base is made of a thermoplastic organic polymer and wherein the receptacle is provided by a thermoformed depression in the base, wherein an upstream terminus of the depression provides the major closed end of the at least one receptacle and wherein a major open end of the depression provides the major open end of the at least one receptacle.

9. The fragrance dispenser of claim 1 wherein the base is made of a thermoplastic molding resin that is at least substantially impermeable to liquids and vapors.

10. The fragrance dispenser of claim 1 wherein:
the base comprises a plurality of receptacles, wherein at least selected receptacles each comprise:
a major closed end and a major open end;
a porous diffuser layer occlusively overlying the major open end of the receptacle;
and, a fragrance source provided within at least a portion of the receptacle,
and,
wherein the fragrance dispenser is positioned so that the at least selected receptacles are proximate the airstream-receiving area of the upstream face of the air filter, with the major closed end of each receptacle facing at least generally upstream and with the major open end of each receptacle facing at least generally downstream toward the upstream face of the filter.

11. The fragrance dispenser of claim 10 wherein the base comprises a thickness and comprises a plurality of through-holes that each extend completely through the thickness of the base so as to permit the flow of air therethrough and wherein at least selected receptacles each comprises an exposed lateral edge over a circumferential extent of the receptacle of at least about 60%.

12. The fragrance dispenser of claim 1 wherein the base comprises a mounting mechanism configured to mount the fragrance dispenser on the air filter so that the at least one receptacle is proximate the airstream-receiving area of the upstream face of the air filter.

13. The fragrance dispenser of claim 12 wherein the base comprises a main body that comprises the at least one receptacle and wherein the base further comprises an extended portion that extends away from the main body and that comprises the mounting mechanism, wherein the mounting mechanism is configured to mount to a perimeter frame of the air filter so as to position the fragrance dispenser so that the at least one receptacle is proximate the airstream-receiving area of the upstream face of the air filter.

14. The fragrance dispenser of claim 13 wherein the extended portion comprises a pressure-sensitive adhesive with a first major side that is adhesively attached to the extended portion and with a second major side that is configured to adhesively attach to an upstream flange of the perimeter frame of the air filter.

15. The fragrance dispenser of claim 13 wherein the extended portion comprises an L-shape with a first portion that extends from the base in a direction at least generally along a major plane of the base, and a second portion that extends from a terminus of the first portion and that is oriented at least generally orthogonally to the first portion, and wherein the second portion comprises a major surface that is configured to abut a sidewall of the perimeter frame of the air filter.

16. The fragrance dispenser of claim 13 wherein the extended portion comprises a U-shape with a first portion that extends from the base in a direction at least generally along a major plane of the base, a second portion that extends from a terminus of the first portion and that has a major plane that is oriented at least generally orthogonally to the first portion, and a third portion that extends from a terminus of the second portion and that has a major plane that is oriented at least generally parallel to a major plane of the first portion,
wherein the second portion comprises a major surface that is configured to abut a sidewall of the perimeter frame of the air filter and wherein the third portion comprises a major surface that is configured to abut a downstream flange of the perimeter frame of the air filter.

17. The fragrance dispenser of claim 1 wherein the fragrance source comprises at least one volatile fragrance that is mixed with at least one non-volatile carrier material, wherein the volatile fragrance comprises at least about 80 wt. % of the fragrance source.

18. The fragrance dispenser of claim 17 wherein the non-volatile carrier material comprises an organic polymeric material.

19. The fragrance dispenser of claim 17 wherein the receptacle and the diffuser layer combine to define a receptacle volume and wherein the fragrance source occupies at least 95% by volume of the receptacle volume.

20. The fragrance dispenser of claim 17 wherein the at least one volatile fragrance and the at least one non-volatile carrier material are mixed with each other to form a solution with substantially no parcels of non-dissolved volatile fragrance being present.

* * * * *

UNITED STATES PATENT AND TRADEMARK OFFICE
CERTIFICATE OF CORRECTION

PATENT NO. : 10,213,519 B2
APPLICATION NO. : 15/325944
DATED : February 26, 2019
INVENTOR(S) : Kannan Seshadri et al.

It is certified that error appears in the above-identified patent and that said Letters Patent is hereby corrected as shown below:

In the Specification

Column 9
Line 1, Delete "that" and insert -- than --, therefor.

Signed and Sealed this
Twenty-fourth Day of September, 2019

Andrei Iancu
*Director of the United States Patent and Trademark Office*